(12) United States Patent
Lo et al.

(10) Patent No.: US 11,896,316 B2
(45) Date of Patent: Feb. 13, 2024

(54) SYSTEMS AND METHODS FOR GENERATING ANATOMIC TREE STRUCTURES USING BACKWARD PATHWAY GROWTH

(71) Applicant: INTUITIVE SURGICAL OPERATIONS, INC., Sunnyvale, CA (US)

(72) Inventors: Pechin Chien Pau Lo, Santa Clara, CA (US); Jun Ma, Santa Clara, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 735 days.

(21) Appl. No.: 16/536,591

(22) Filed: Aug. 9, 2019

(65) Prior Publication Data

US 2020/0060771 A1    Feb. 27, 2020

Related U.S. Application Data

(60) Provisional application No. 62/721,954, filed on Aug. 23, 2018.

(51) Int. Cl.
*A61B 34/20* (2016.01)
*A61B 34/00* (2016.01)
(Continued)

(52) U.S. Cl.
CPC ............. *A61B 34/20* (2016.02); *A61B 34/25* (2016.02); *A61B 90/37* (2016.02); *G06T 7/0012* (2013.01);
(Continued)

(58) Field of Classification Search
CPC ......... A61B 34/20; A61B 34/25; A61B 90/37; A61B 2034/105; A61B 2034/301;
(Continued)

(56) References Cited

U.S. PATENT DOCUMENTS 6,380,732 B1    4/2002  Gilboa
6,389,187 B1    5/2002  Greenaway et al.
(Continued)

FOREIGN PATENT DOCUMENTS

WO    WO-2016191298 A1    12/2016

OTHER PUBLICATIONS

Lo P, Sporring J, Pedersen JJ, de Bruijne M. Airway tree extraction with locally optimal paths. Med Image Comput Comput Assist Interv. 2009;12(Pt 2):51-8. doi: 10.1007/978-3-642-04271-3_7. PMID: 20426095. (Year: 2009).*

(Continued)

*Primary Examiner* — Boniface Ngathi
*Assistant Examiner* — Zainab Mohammed Aldarraji
(74) *Attorney, Agent, or Firm* — Haynes & Boone, LLP.

(57) ABSTRACT

A method includes receiving anatomic image data comprising a plurality of graphical units; generating an initial segmented set of the plurality of graphical units associated with an anatomic tree structure; receiving an indication of a first user selected graphical unit, the first user selected graphical unit being outside the initial segmented set of the plurality of graphical units; applying a cost function to determine a first sequence of graphical units from the first user selected graphical unit to the initial segmented set of graphical units; receiving an indication of a second user selected graphical unit, the second user selected graphical unit being selected from the first sequence of the plurality of graphical units; and applying the cost function to determine a second sequence of the plurality of graphical units from the (Continued)

second user selected graphical unit to the initial segmented set of the plurality of graphical units.

16 Claims, 8 Drawing Sheets

(51) Int. Cl.
| | |
|---|---|
| *G06T 7/00* | (2017.01) |
| *G06T 7/10* | (2017.01) |
| *G06T 17/00* | (2006.01) |
| *A61B 90/00* | (2016.01) |
| *A61B 34/30* | (2016.01) |
| *A61B 34/10* | (2016.01) |

(52) U.S. Cl.
CPC ............... *G06T 7/10* (2017.01); *G06T 17/00* (2013.01); *A61B 2034/105* (2016.02); *A61B 2034/301* (2016.02); *A61B 2090/374* (2016.02); *A61B 2090/378* (2016.02); *A61B 2090/3735* (2016.02); *A61B 2090/3762* (2016.02); *G06T 2207/30004* (2013.01)

(58) Field of Classification Search
CPC ...... A61B 2090/3735; A61B 2090/374; A61B 2090/3762; A61B 2090/378; A61B 34/37; A61B 34/30; A61B 2034/2051; A61B 2034/2059; A61B 2034/2061; G06T 7/0012; G06T 7/10; G06T 17/00; G06T 2207/30004; G06T 2207/10081; G06T 2207/10088; G06T 2207/30061; G06T 2210/41; G06T 7/11; G06T 7/187
See application file for complete search history.

(56) References Cited

U.S. PATENT DOCUMENTS

| | | | |
|---|---|---|---|
| 7,316,681 B2 | 1/2008 | Madhani et al. | |
| 7,772,541 B2 | 8/2010 | Froggatt et al. | |
| 8,147,503 B2* | 4/2012 | Zhao | A61B 34/37 |
| | | | 382/128 |
| 9,259,274 B2 | 2/2016 | Prisco | |
| 9,452,276 B2 | 9/2016 | Duindam et al. | |
| 10,430,949 B1* | 10/2019 | Wang | G06T 7/0012 |
| 10,643,333 B2* | 5/2020 | Dougherty | G06T 17/005 |
| 10,909,684 B2* | 2/2021 | Saha | G16H 50/20 |
| 2006/0013523 A1 | 1/2006 | Childlers et al. | |
| 2009/0185731 A1* | 7/2009 | Ray | G06T 7/12 |
| | | | 382/131 |
| 2014/0081129 A1* | 3/2014 | Lu | G06T 7/0012 |
| | | | 600/424 |
| 2016/0070878 A1* | 3/2016 | Soper | A61B 34/10 |
| | | | 703/11 |
| 2018/0240235 A1* | 8/2018 | Mazo | G06N 3/04 |
| 2020/0054399 A1 | 2/2020 | Duindam et al. | |
| 2022/0054202 A1* | 2/2022 | Soper | A61B 1/00006 |
| 2022/0092786 A1* | 3/2022 | Xu | G06T 7/11 |

OTHER PUBLICATIONS

Petersen J,. Optimal surface segmentation using flow lines to quantify airway abnormalities in chronic obstructive pulmonary disease. Med Image Anal. Apr. 2014;18(3):531-41. doi: 10.1016/j.media.2014.02.004. Epub Feb. 17, 2014. (Year: 2014).*

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR GENERATING ANATOMIC TREE STRUCTURES USING BACKWARD PATHWAY GROWTH

CROSS-REFERENCE TO RELATED APPLICATIONS

This application claims the benefit of U.S. Provisional Application 62/721,954 filed Aug. 23, 2018, which is incorporated by reference herein in its entirety.

TECHNICAL FIELD

The present disclosure is directed to systems and methods for generating anatomic tree structures and more particularly to systems and methods for backward growth of anatomic branch pathways toward an anatomic tree structure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Navigation may be assisted through the use of images of the anatomic passageways. Improved systems and techniques are needed to accurately perform image segmentation, using both auto-segmentation techniques and user inputs, to accurately generate anatomic tree structures that correspond to the patient's anatomic passageways.

SUMMARY

The embodiments of the invention are best summarized by the claims that follow the description.

In one example, a method comprises receiving anatomic image data comprising a plurality of graphical units and generating an initial segmented set of the plurality of graphical units associated with an anatomic tree structure. The method also comprises receiving an indication of a first user selected graphical unit from the plurality of graphical units and applying a cost function to determine a first sequence of the plurality of graphical units from the first user selected graphical unit to the initial segmented set of the plurality of graphical units.

In one example, a system for modeling an anatomic tree structure comprises a display system and a control system communicatively coupled to the display system. The control system is configured to receive anatomic image data comprising a plurality of graphical units and generate an initial segmented set of the plurality of graphical units associated with the anatomic tree structure. The control system is also configured to receive an indication of a first user selected graphical unit from the plurality of graphical units and apply a cost function to determine a first sequence of the plurality of graphical units from the first user selected graphical unit to the initial segmented set of the plurality of graphical units.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Examples of techniques disclosed in this patent document can be used to implement segmentation of tree structures that represent anatomical pathways in medical images. The segmented tree structures as created using the disclosed techniques can be used to enable navigation of medical instruments within the anatomical pathways.

The disclosed techniques for segmenting tree structures in medical images can enable manually segmenting beyond the main trunks of the tree structures to grow out smaller and more distal branches that may be missed by automated algorithms. Manually growing the smaller and more distal branches can be performed by growing forward starting from the end of current segmentation and extending further forward to connect to even smaller and more distal branches. In another aspect, manually growing the smaller and more distal branches can be performed by growing backwards from a point that is not part of the tree structure and connecting it back to the nearest segmented tree structure. By growing backwards, a user can identify a target (e.g., a cancer nodule) and elect to grow pathways near the target back to the currently segmented tree structure. This allows the user to selectively grow additional smaller and more distal pathways as needed to navigate to the desired target without needing to grow out tree structure in areas unrelated to the desired target.

Figure 1:
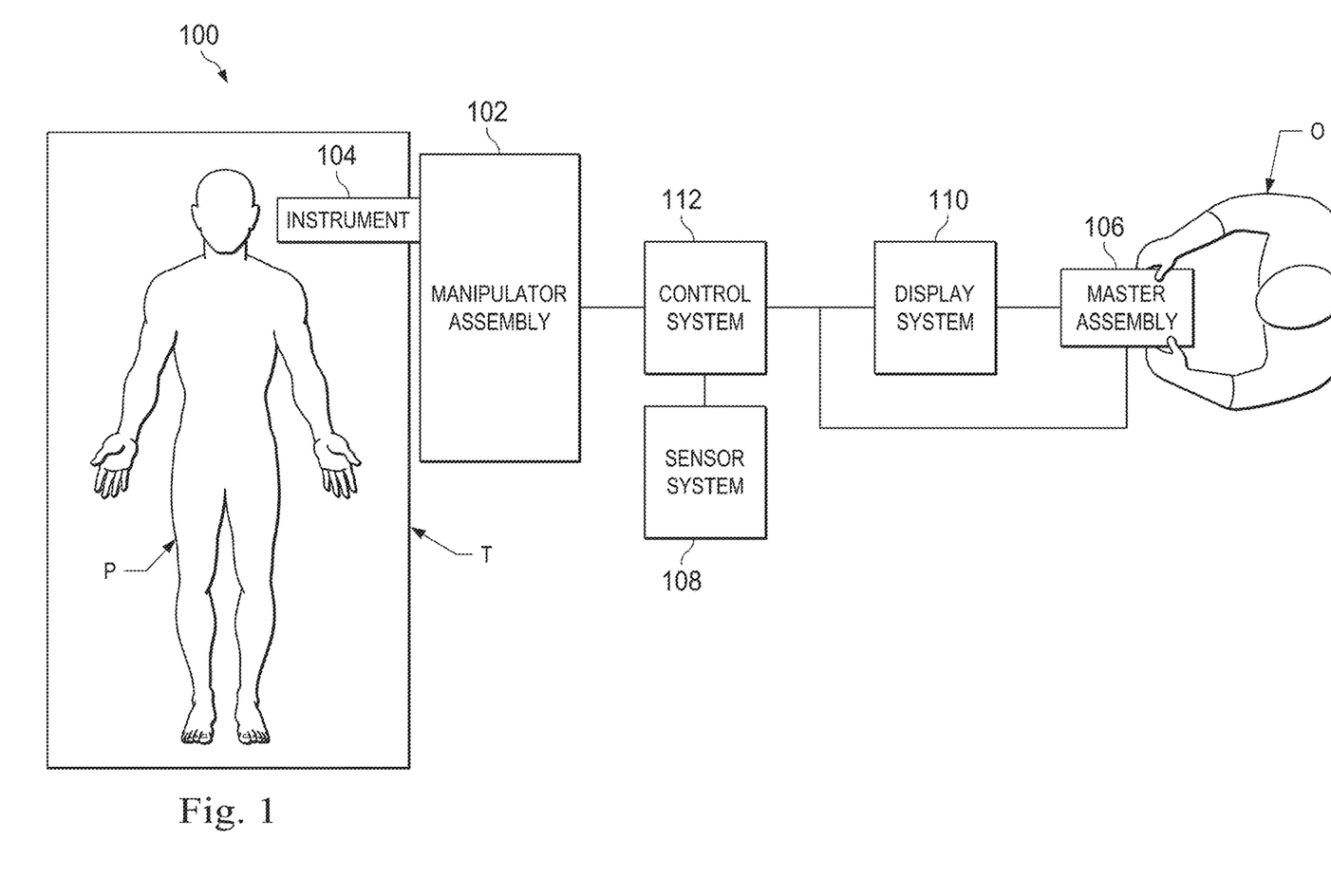
FIG. 1 is a simplified diagram of a teleoperated medical system according to some embodiments.

FIG. 1 is a diagram of an exemplary medical system 100 that can be used to implement the disclosed techniques for growing tree structures. As shown in FIG. 1, medical system 100 generally includes a manipulator assembly 102 for operating a medical instrument 104 in performing various procedures on a patient P. Medical instrument 104 may extend into an internal surgical site within the body of patient P via an opening in the body of patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like.

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like.

Medical system 100 may include a sensor system 108 with one or more sub-systems for receiving information about the manipulator assembly 102 and/or the medical instrument 104. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; a visualization system for capturing images from the distal end of medical instrument 104; and actuator position sensors such as resolvers, encoders, potentiometers, and the like that describe the rotation and orientation of the motors controlling the instrument 104.

Medical system 100 also includes a display system 110 for displaying an image or representation of the surgical site and medical instrument 104. Display system 110 and master assembly 106 may be oriented so operator O can control medical instrument 104 and master assembly 106 with the perception of telepresence.

In some embodiments, medical instrument 104 may include a visualization system which may include an image capture assembly that records a concurrent or real-time images of a surgical site and provides the image to the operator O through one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of image-guided medical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104.

Medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104.

Control system 112 may optionally further include a virtual visualization system to provide navigation assistance to operator O when controlling medical instrument 104 during an image-guided medical procedure. Virtual navigation using the virtual visualization system may be based upon reference to an acquired preoperative or intraoperative dataset of anatomic passageways. Software, which may be used in combination with operator inputs, is used to convert the recorded images into segmented two dimensional or three dimensional composite representation of a partial or an entire anatomic organ or anatomic region. An image data set is associated with the composite representation. The virtual visualization system obtains sensor data from sensor system 108 that is used to compute an approximate location of medical instrument 104 with respect to the anatomy of patient P. The system may implement the sensor system 108 to register and display the medical instrument together with the preoperatively or intraoperatively recorded surgical images. For example, PCT Publication WO 2016/191298 (published Dec. 1, 2016) (disclosing "Systems and Methods of Registration for Image Guided Surgery"), which is incorporated by reference herein in its entirety, discloses such one system.

Medical system 100 may further include optional operations and support systems (not shown) such as illumination systems, steering control systems, irrigation systems, and/or suction systems. In some embodiments, medical system 100 may include more than one manipulator assembly and/or more than one master assembly. The exact number of teleoperational manipulator assemblies will depend on the medical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
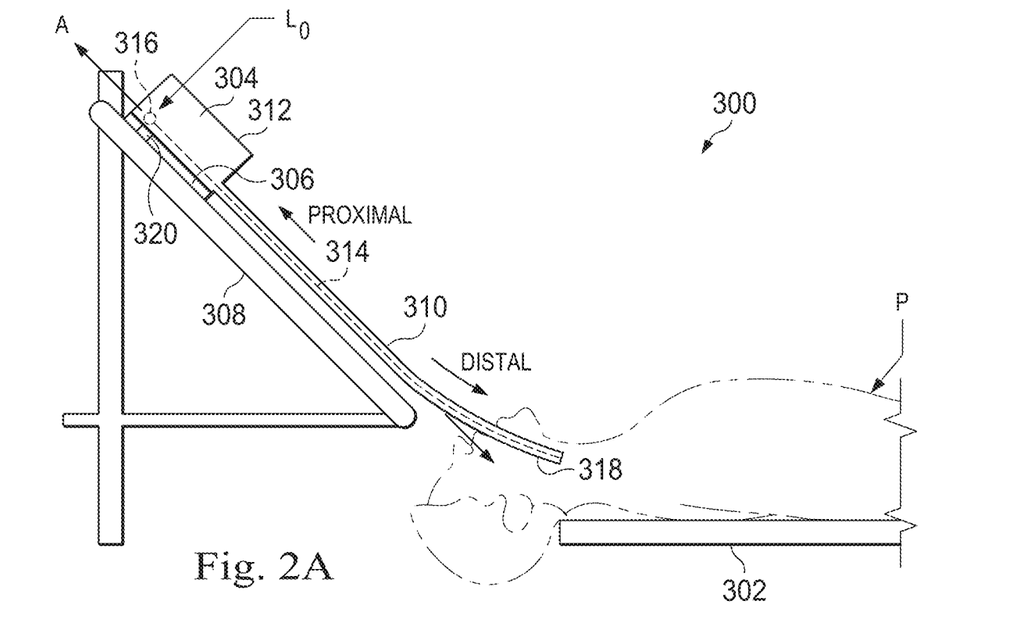
FIGS. 2A and 2B are simplified diagrams of side views of a patient coordinate space including a medical instrument mounted on an insertion assembly according to some embodiments.
Figure 2B:
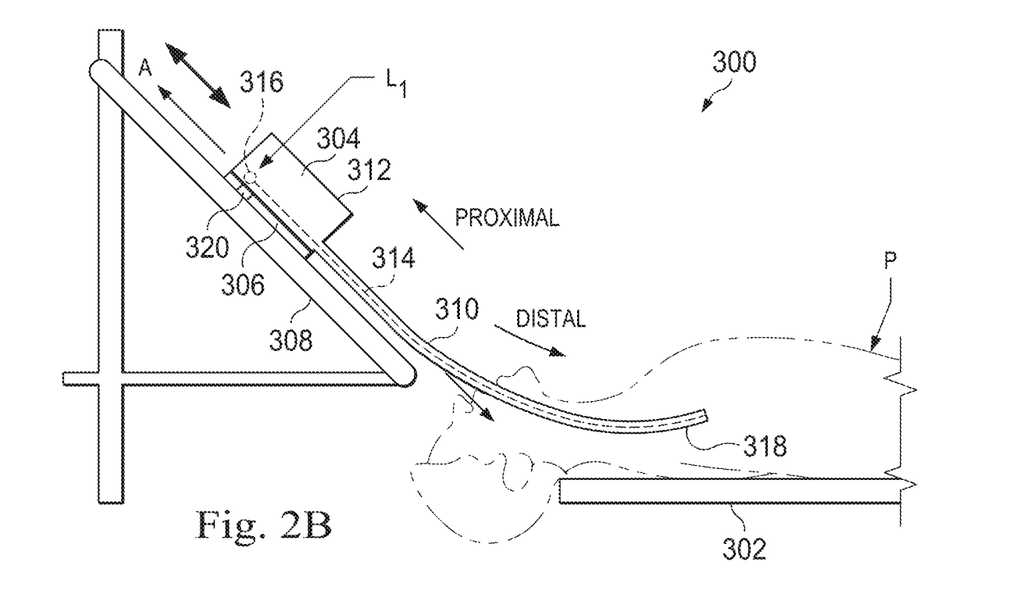

FIGS. 2A and 2B are simplified diagrams of side views of a patient coordinate space including a medical instrument mounted on an insertion assembly according to some embodiments. As shown in FIGS. 2A and 2B, a surgical environment 300 including a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue. Within surgical environment 300, a medical instrument 304 is used to perform a medical procedure which may include, for example, surgery, biopsy, ablation, illumination, irrigation, suction, or a system registration procedure. The medical instrument 304 may be, for example, the instrument 104. The instrument 304 includes a flexible elongate device 310 (e.g., a catheter) coupled to an instrument body 312. Elongate device 310 includes one or more channels (not shown) sized and shaped to receive a medical tool (not shown).

Elongate device 310 may also include one or more sensors (e.g., components of the sensor system 108). In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Shape sensor 314 may be aligned with flexible elongate device 310 (e.g., provided within an interior channel (not shown) or mounted externally). In one embodiment, the optical fiber has a diameter of approximately 200 μm. In other embodiments, the dimensions may be larger or smaller. The shape sensor 314 may be used to determine the shape of flexible elongate device 310. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. Various systems for using fiber optic sensors to register and display a surgical instrument with surgical images are provided in PCT Publication WO 2016/191298 (published Dec. 1, 2016) (disclosing "Systems and Methods of Registration for Image Guided Surgery"), which is incorporated by reference herein in its entirety.

In various embodiments, position sensors such as electromagnetic (EM) sensors, may be incorporated into the medical instrument 304. In various embodiments, a series of position sensors may be positioned along flexible body 216 and then used for shape sensing. In some embodiments, position sensors may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

Elongate device 310 may also house cables, linkages, or other steering controls (not shown) that extend between instrument body 312 and distal end 318 to controllably bend distal end 318. In some examples, at least four cables are used to provide independent "up-down" steering to control a pitch of distal end 318 and "left-right" steering to control a yaw of distal end 318. Steerable elongate devices are described in detail in U.S. patent application Ser. No. 13/274,208 (filed Oct. 14, 2011) (disclosing "Catheter with Removable Vision Probe"), which is incorporated by reference herein in its entirety. The instrument body 312 may include drive inputs that removably couple to and receive power from drive elements, such as actuators, of the teleoperational assembly.

Instrument body 312 may be coupled to instrument carriage 306. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to medical instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

A sensor device 320, which may be a component of the sensor system 108, provides information about the position of instrument body 312 as it moves on insertion stage 308 along an insertion axis A. Sensor device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 2A shows instrument body 312 and instrument carriage 306 in a retracted position along insertion stage 308. In this retracted position, the proximal point 316 is at a position $L_0$ on axis A. In this position along insertion stage 308, the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, sensor device 320 may be set to a zero and/or another reference value (e.g., I=0). In FIG. 2B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

In an illustrative application, a medical system, such as medical system 100, may include a robotic catheter system for use in lung biopsy procedures. A catheter of the robotic catheter system provides a conduit for tools such as endoscopes, endobronchial ultrasound (EBUS) probes, and/or biopsy tools to be delivered to locations within the airways where one or more anatomic targets of the lung biopsy, such as lesions, nodules, tumors, and/or the like, are present. When the catheter is driven through anatomy, typically an endoscope is installed such that a clinician, such as surgeon O, can monitor a live camera feed of a distal end of the catheter. The live camera feed and/or other real-time navigation information may be displayed to the clinician via a graphical user interface. An example of a graphical user interface for monitoring the biopsy procedure is covered in U.S. Provisional Patent Application No. 62/486,879, entitled "Graphical User Interface for Monitoring an Image-Guided Procedure and filed Apr. 18, 2017, which is hereby incorporated by reference in its entirety.

As described above, the virtual visualization system processes preoperative or intra-operative images of the patient anatomy using software to convert the recorded images into an anatomic image data set and then into segmented two dimensional or three dimensional composite representations of a partial or an entire anatomic organ or anatomic region. Anatomic image data of some branched anatomic structures, such as lung airways or blood vessels, may form segmented anatomic tree models. Although segmentation algorithms may be effective to segment larger anatomic structures, such as the main trunks of anatomic trees, smaller and more distal branches may be more effectively segmented based on user inputs, particularly if branch extension and segmentation are needed only in specific regions. For example, in planning a lung biopsy procedure, segmentation of the main trunk of the airway may be performed by segmentation algorithms, and more distal branches may be identified for segmentation and added to the main trunk based on user-identified (and algorithmically unsegmented) airways near the location of the biopsy target structure. Purely manual tracing of user-identified branches may be time consuming and tedious, requiring a user to navigate between multiple anatomic image slices. The systems and methods described below may be used to more efficiently generate accurate anatomic tree models using both segmentation computations and user inputs to add distal branches to anatomic trunk models.

Figure 3:
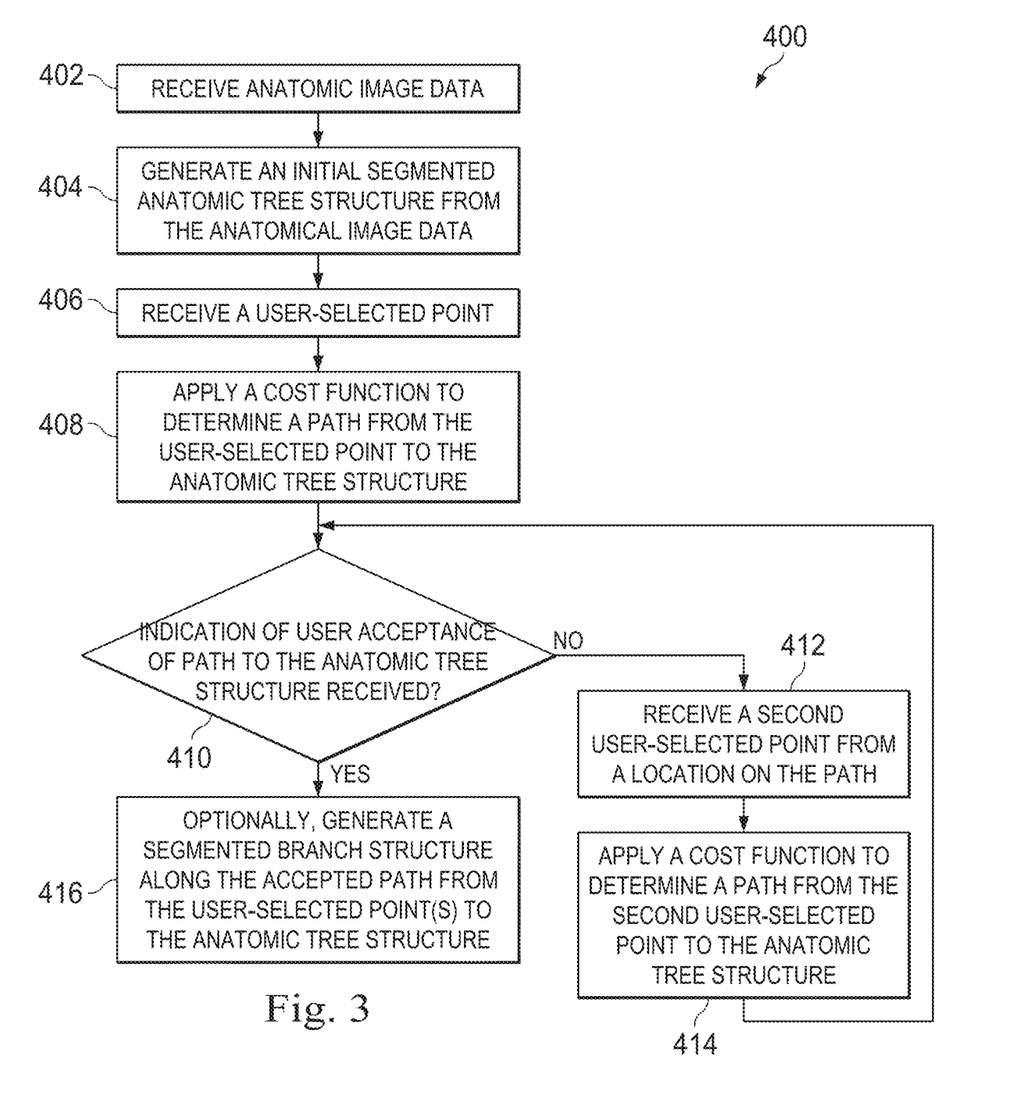
FIG. 3 illustrates a method for generating an anatomic branch model from anatomic image data.

FIG. 3 illustrates a method 400 for generating an anatomic branch model from anatomic image data. The method 400 is illustrated as a set of operations or processes 402 through 416 and is described with continuing reference to FIGS. 4-8. Not all of the illustrated processes 402 through 416 may be performed in all embodiments of method 400. Additionally, one or more processes that are not expressly illustrated in FIG. 4 may be included before, after, in between, or as part of the processes 402 through 416. In some embodiments, one or more of the processes 402 through 416 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 402 through 416 may be performed by the control system 112.

At a process 402, anatomic image data is received. The anatomic image data may be digital image data and may be recorded pre-operatively or intra-operatively using imaging technology such as CT, MRI, fluoroscopy, and/or the like. The pre-operative or intra-operative image data may be used to generate two-dimensional, three-dimensional, or four-dimensional (including e.g., time based or velocity based information) images. The image data may describe the various locations and shapes of anatomic passageways and their connectivity. The anatomic image data may be received at the control system 112 or at another processor used to perform graphical segmentation with the image data.

Figure 4:
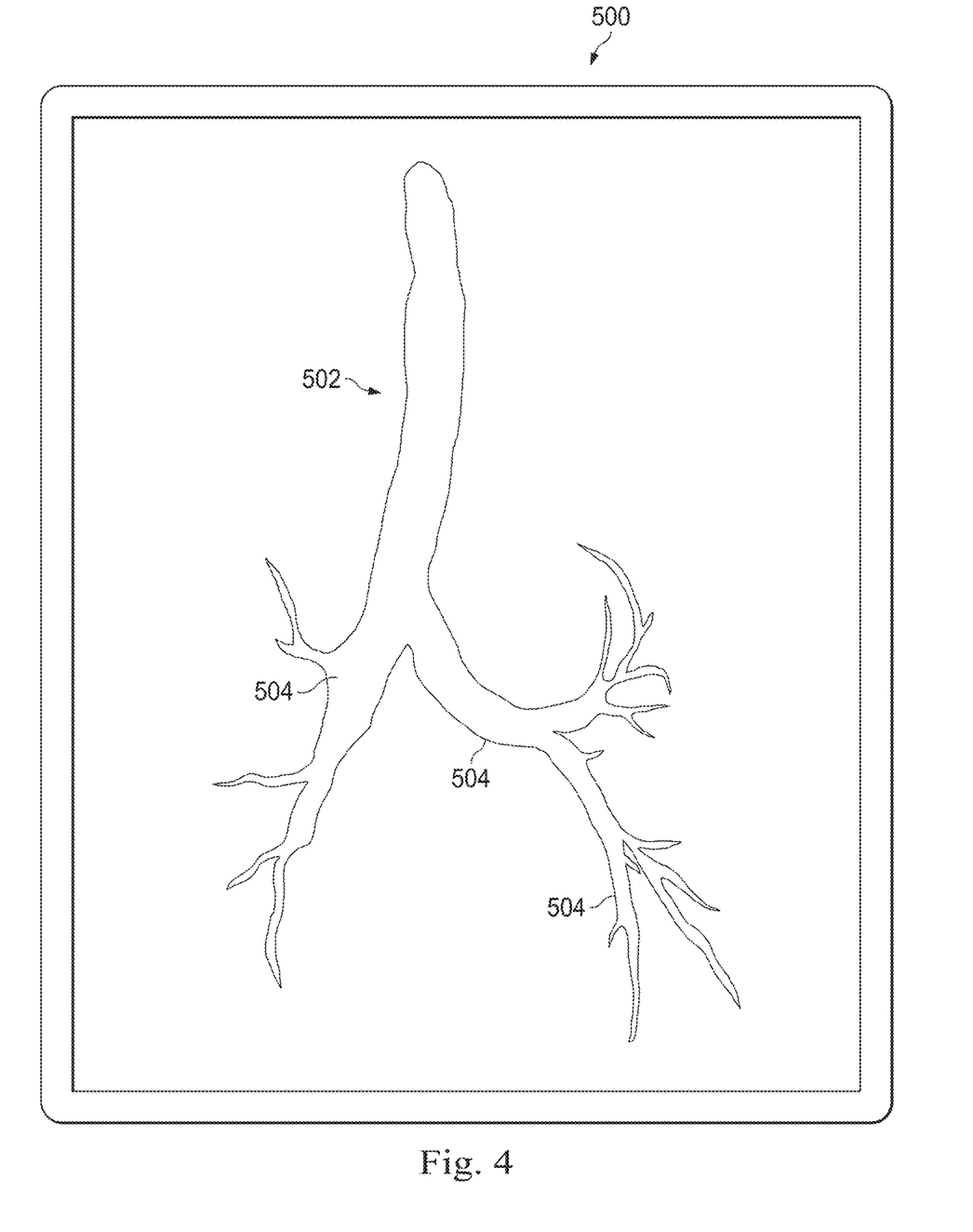
FIG. 4 illustrates a display including a segmented anatomic tree structure generated from anatomic image data.

At a process 404, an initial segmented anatomic tree structure is generated from the anatomical image data. The process 404 includes growing an initial segmented set, such as a main trunk portion of the anatomic tree structure, by applying the image segmentation algorithm to partition the digital image data into graphical units (e.g., pixels or voxels). The segmentation may be generated from an initial graphical unit (e.g., a voxel) from the image data or in a probability map. In various examples, the chosen initial graphical unit may be a voxel associated with the trachea in a set of lung image data. The trachea voxel provides a seed to the segmentation algorithm which then evaluates neighboring voxels against a threshold value to determine whether the neighboring voxels should be included in the main trunk model. In various examples, the trachea voxel may have a Hounsfield value greater than −500 HU. Neighboring voxels to the trachea voxel may be added to the main trunk model if they are less than a threshold of, for example −500 HU. In the example of the lung image data, the threshold value may be set so that the main trunk model captures only the trachea, the main bronchi, and potentially other relatively large airways. With reference to FIG. 4, a display 500 (e.g., on a display system 110) shows a main trunk model 502 with a plurality of branches 504 formed from the segmentation of the image data. The branches 504 in the main trunk model 502 may all be coupled to the main trunk model, with no orphan branches.

In one example embodiment, growing a main trunk of an anatomical branch model includes smoothing the anatomical image data to reduce noise. An initial graphical unit (i.e., a seed) from the smoothed anatomical image data may be grown by gradually increasing the threshold from the lowest value in the image up to a threshold of approximately 500 HU. The growing process may be stopped if no more neighboring voxels with values less than the threshold exist and the maximum threshold of −500 HU has been reached. The growing process may also be stopped if the distance from the seed voxel to the current accepted voxel exceeds a certain distance (e.g., 1000 mm). The growing process may also be stopped if the total volume of grown voxels exceeds a threshold value such as approximately 57,000 cu. mm.

Figure 5:
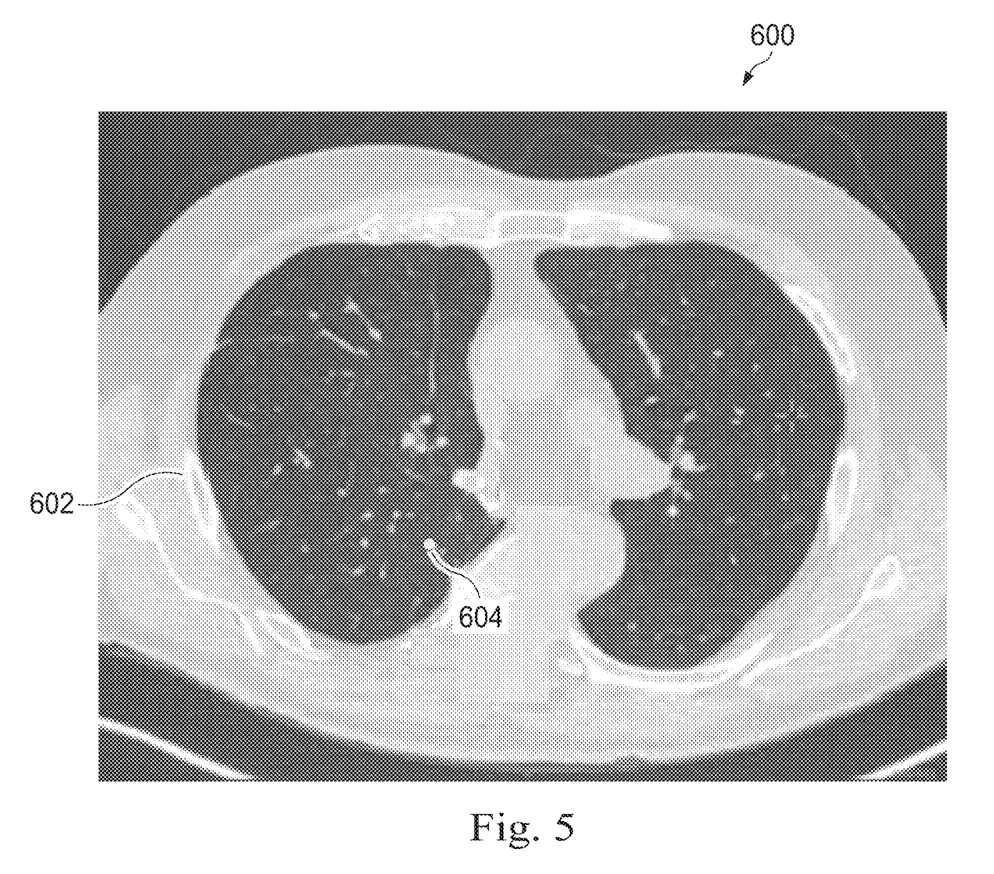
FIG. 5 illustrates a display including an anatomic scan image.

The initial algorithm-based segmentation process 404 may fail to segment smaller and more distal branches of the anatomic image data. If tissue of interest (for example, a target tissue for a biopsy procedure) is located in an area of the anatomic structure that has not been segmented by the initial algorithm, the initial segmentation process may be supplemented by user-inputs to help identify anatomic branches near the target tissue. At a process 406, a user-selected point is received to initiate a backward path to the initial segmented anatomic tree (e.g., segmented main trunk model 502). The user-selected point may be associated with one or more graphical units of the image data set. The user-selected point may be identified in an anatomic image near a tissue of interest, such as a biopsy target. For example, a user may use an operator input device such as a touchscreen, a stylet, or a mouse to identify a point visible to user in a CT scan. With reference to FIG. 5, a CT image 600 of lung tissue 602 is marked with a user-selected point 604. The point 604 may be along an airway near a target tissue such as a lung nodule.

Figure 7:
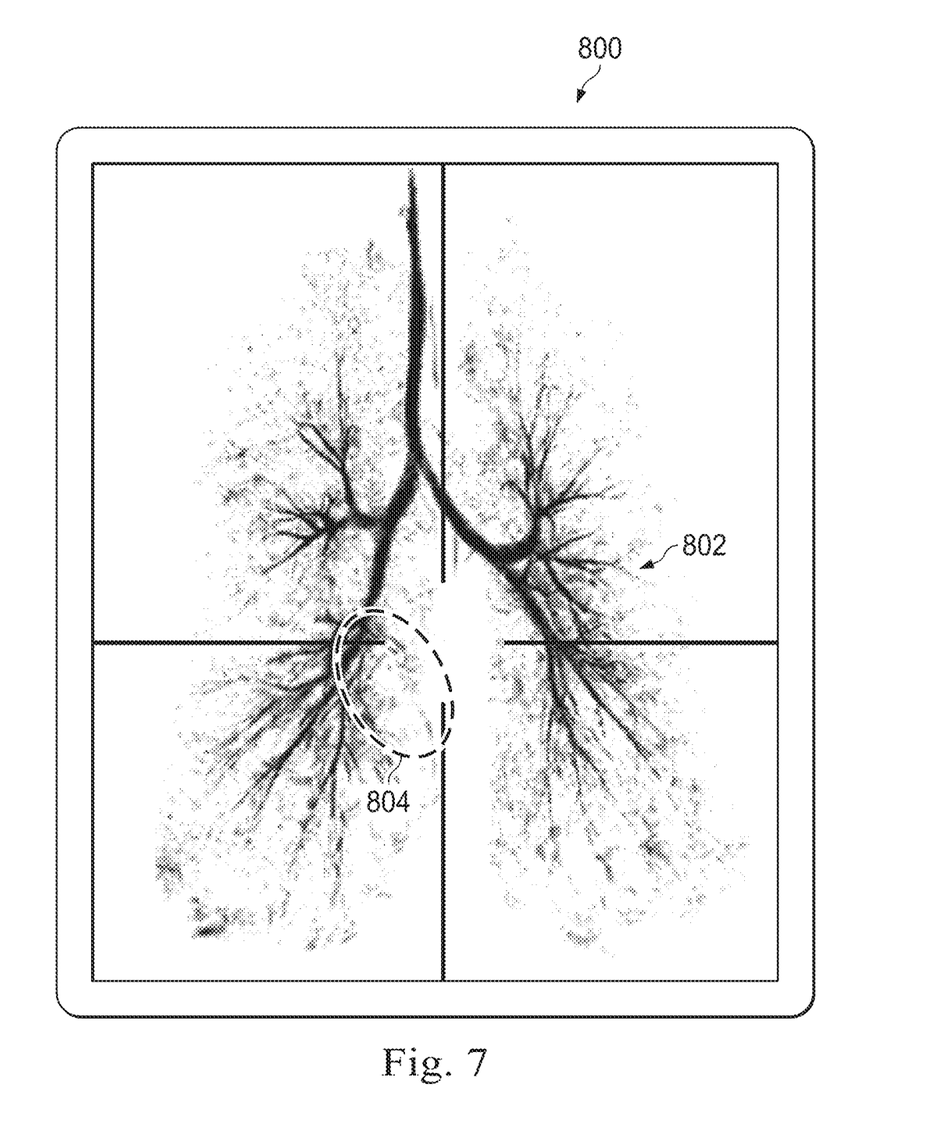
FIG. 7 illustrates a display including a probability map for a set of anatomic image data.
Figure 8:
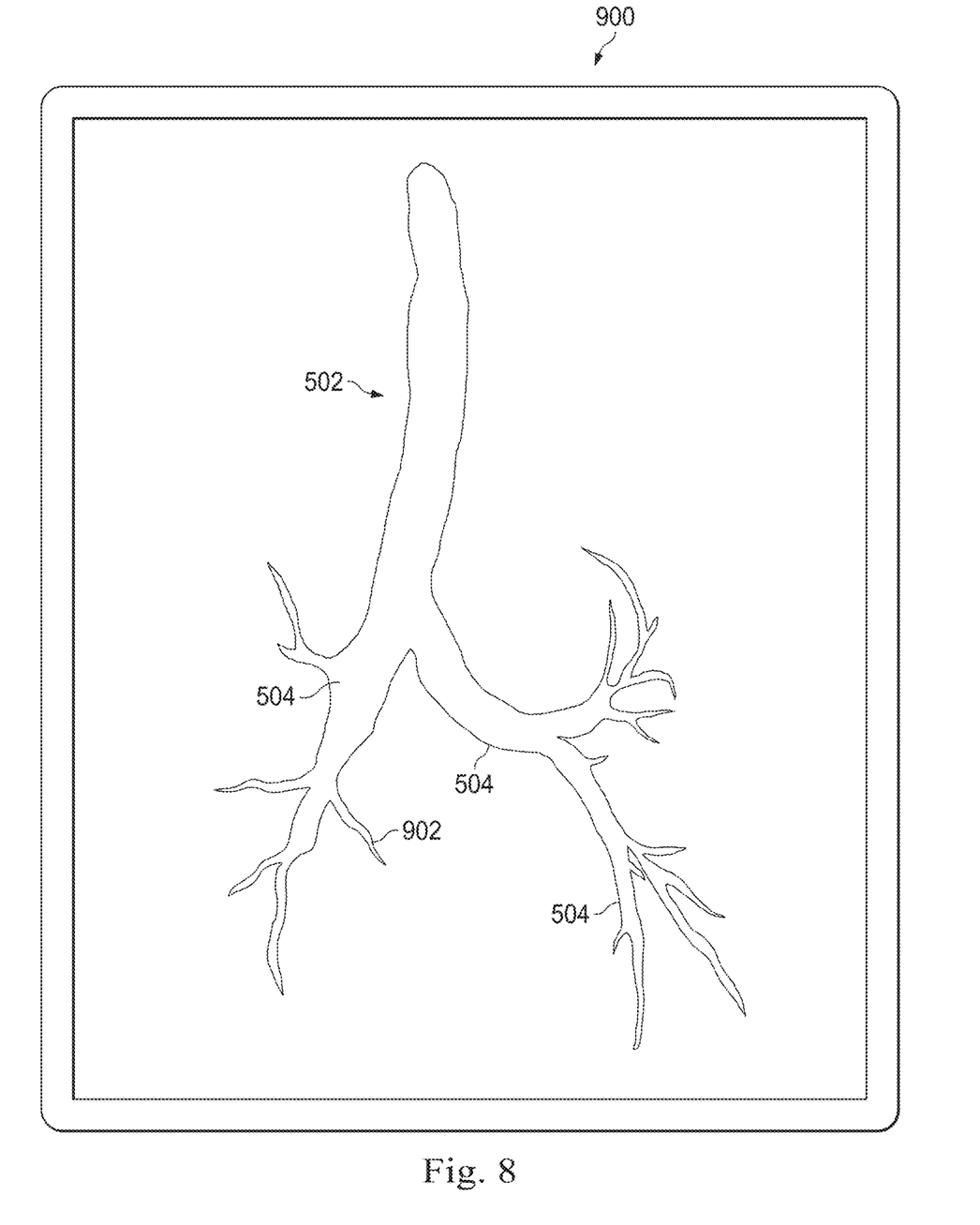
FIG. 8 illustrates a display including the segmented anatomic tree structure of FIG. 4 updated with a supplemented branch based on the user-selected points.

At a process 408, a cost function is applied to determine a path from the user-selected point to the anatomic tree structure. The path may be an optimized path computed, for example, by determining a minimum cost using the Dijkstra algorithm with a cost function that may include factors such as distance from the user-selected point to the anatomic tree structure, graphical unit probability based for example on a probability map, smoothing filters, and/or other cost function inputs. In greater detail, the probability map associates a probability value with each graphical unit. The probability value may correspond to a type of anatomic tissue or structure. If, for example, the anatomic structure is a lung, the probability value may correspond to soft tissue or to airways. FIG. 7 illustrates a display 800 including a probability map 802 for a set of anatomic image data. The probability map may be derived from, for example, a filter response (such as a tube filter response), the use of a classifier, or semantic segmentation using a convolutional neural network.

Figure 6:
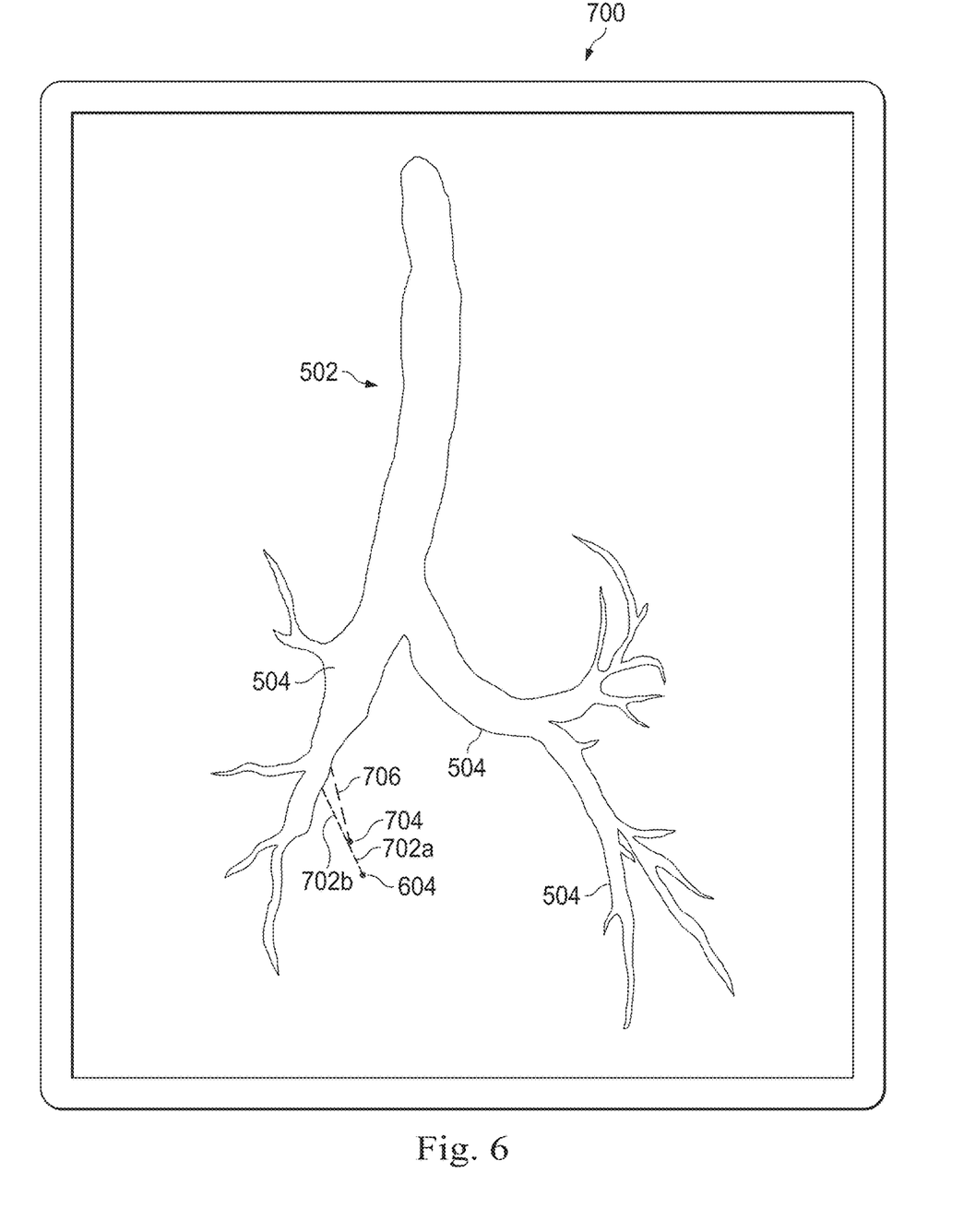
FIG. 6 illustrates a display with paths between user-selected points and the segmented anatomic tree structure of FIG. 4.

The path determined by the cost function may be comprised of a sequence of graphical units that correspond to a centerline of an anatomic passage from the user-selected point to the anatomic tree structure. With reference to FIG. 6, a path including path segments 702a, 702b is shown between the user-selected point 604 and the branch 504 of the main trunk 502. The path 702 may be determined, for example, using a cost function considering such factors as a distance between the point 604 and the closest segmented branch 504 and probability values from the associated region 804 of the probability map 802.

At a process 410, a determination is made as to whether an indication of user acceptance of the path to the anatomic tree structure has been received. The user may evaluate the path (e.g. the path 702a/702b) by reviewing an image of the path overlaid on one or more anatomic images (e.g., CT images). Additionally or alternatively, the three-dimensional nature of the path may be evaluated by scrolling through multiple sequential anatomic images to determine whether the generated path tracks the anatomic passageway visible to the user in the anatomic images. If the generated path appears acceptable to the user along the entire length of the path, the user may provide an input indicating acceptance (e.g., an input received at a mouse, a touchpad, a button) and the method proceeds to a process 416. If the path is unacceptable to the user because, for example, it diverges from the anatomic passageway visible to the user in the anatomic images, the method proceeds to a process 412.

At the process 412, a second user-selected point is received to initiate a path to the initial segmented anatomic tree. The second user-selected point is chosen from a location along the path 702a/702b. With reference to FIG. 6, a second user-selected point 704 is selected from the path 702a/702b. The point 704 may be, for example, the user-observed point at which the path 702a diverges from the anatomic pathway visible to the user in the anatomic images.

At a process 414, a cost function is applied to determine a path from the second user-selected point (e.g. point 704) to the anatomic tree structure. The path may be an optimized path computed, for example, by determining a minimum cost using the Dijkstra algorithm with a cost function that may include factors such as distance from the second user-selected point to the anatomic tree structure, graphical unit probability based for example on the probability map, smoothing filters, and/or other cost function inputs. The path determined by the cost function may be comprised of graphical units that correspond to a centerline of the anatomic passage from the second user-selected point to the anatomic tree structure. With reference to FIG. 6, a path 706 is shown between the second user-selected point 704 and the branch 504 of the main trunk 502. The path 704 may be determined, for example, using a cost function considering such factors as a distance between the point 704 and the closest segmented branch 504 and probability values as illustrated in a probability map 802. The method proceeds again to process 410 where a determination is made as to whether an indication of user acceptance of the path to the anatomic tree structure has been received. The processes 410, 412, 414 may be repeated until an indication of user acceptance of the path is received. The final path may be a path through multiple user selected points between the initial point 604 and the branch 504 with each sequential point chosen from the path between the preceding point and the branch 504. For example, in FIG. 6, the final path may be the path 702a, 706 through the points 604, 704 to the branch 504.

Optionally, at the process 416, after the user has indicated acceptance of a path, a branch structure may be segmented along the accepted path from the user-selected point(s) to the anatomic tree structure. For example, with reference to FIG. 8, a display 900 includes the main trunk 502 supplemented with a branch 902 that is comprised of a set of graphical units segmented around the path though user-selected points 604, 704. Thus a full three-dimensional model of navigable airways from the patient's trachea to the target area of interest may be efficiently segmented using both segmentation algorithms and user-input points.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

Various instruments and portions of instruments have been described in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
receiving anatomic image data comprising a plurality of graphical units;
generating an initial segmented set of the plurality of graphical units associated with an anatomic tree structure;
receiving an indication of a first user selected graphical unit from the plurality of graphical units, the first user selected graphical unit being outside the initial segmented set of the plurality of graphical units;
applying a cost function to determine a first sequence of the plurality of graphical units from the first user selected graphical unit outside the initial segmented set to the initial segmented set of the plurality of graphical units;

receiving an indication of a second user selected graphical unit from the plurality of graphical units, the second user selected graphical unit being selected from the first sequence of the plurality of graphical units; and applying the cost function to determine a second sequence of the plurality of graphical units from the second user selected graphical unit to the initial segmented set of the plurality of graphical units.

2. The method of claim 1 further comprising:

determining a path through the first and second user selected graphical units to the initial segmented set of the plurality of graphical units.

3. The method of claim 2 further comprising:

supplementing the initial segmented set of the plurality of graphical units with a branch segmented set of the plurality of graphical units based on the path; and generating a three-dimensional model of the anatomic tree structure from the initial segmented set and branch segmented sets of the plurality of graphical units.

4. The method of claim 1 further comprising:

displaying the first sequence of the plurality of graphical units overlaid on an image generated from the anatomic image data.

5. The method of claim 1 further comprising:

segmenting a supplemental set of the plurality of graphical units near the first sequence of the plurality of graphical units, the supplemental set of the plurality of graphical units associated with the anatomic tree structure.

6. The method of claim 1 wherein applying the cost function to determine the first sequence includes evaluating a plurality of graphical unit probability values to determine the first sequence of the plurality of graphical units from the first user selected graphical unit to the initial segmented set of the plurality of graphical units.

7. The method of claim 1 wherein applying the cost function to determine the first sequence includes evaluating a plurality of graphical unit distance values to determine the first sequence of the plurality of graphical units from the first user selected graphical unit to the initial segmented set of the plurality of graphical units.

8. The method of claim 1 further comprising receiving an indication of a user acceptance of the second sequence of the plurality of graphical units.

9. A system for modeling an anatomic tree structure, the system comprising:

a display system; and a control system communicatively coupled to the display system, wherein the control system is configured to:

receive anatomic image data comprising a plurality of graphical units;

generate an initial segmented set of the plurality of graphical units associated with the anatomic tree structure;

receive an indication of a first user selected graphical unit from the plurality of graphical units, the first user selected graphical unit being outside the initial segmented set of the plurality of graphical units;

apply a cost function to determine a first sequence of the plurality of graphical units from the first user selected graphical unit outside the initial segmented set to the initial segmented set of the plurality of graphical units;

receive an indication of a second user selected graphical unit from the plurality of graphical units, the second user selected graphical unit being selected from the first sequence of the plurality of graphical units; and apply the cost function to determine a second sequence of the plurality of graphical units from the second user selected graphical unit to the initial segmented set of the plurality of graphical units.

10. The system of claim 9 wherein the control system is further configured to:

determine a path between the first and second user selected graphical units.

11. The system of claim 10 wherein the control system is further configured to:

supplement the initial segmented set of the plurality of graphical units with a branch segmented set of the plurality of graphical units based on the path; and generate a three-dimensional model of the anatomic tree structure from the initial segmented set and branch segmented sets of the plurality of graphical units for display on the display system.

12. The system of claim 9 wherein the control system is further configured to:

display the first sequence of the plurality of graphical units overlaid on an image generated from the anatomic image data on the display system.

13. The system of claim 9 wherein the control system is further configured to:

segment a supplemental set of the plurality of graphical units near the first sequence of the plurality of graphical units, the supplemental set of the plurality of graphical units associated with the anatomic tree structure.

14. The system of claim 9 wherein applying the cost function to determine the first sequence includes evaluating a plurality of graphical unit probability values to determine the first sequence of the plurality of graphical units from the first user selected graphical unit to the initial segmented set of the plurality of graphical units.

15. The system of claim 9 wherein applying the cost function to determine the first sequence includes evaluating a plurality of graphical unit distance values to determine the first sequence of the plurality of graphical units from the first user selected graphical unit to the initial segmented set of the plurality of graphical units.

16. The system of claim 9 wherein the control system is further configured to receive an indication of a user acceptance of the second sequence of the plurality of graphical units.

* * * * *